United States Patent
Peterman et al.

(10) Patent No.: US 7,291,164 B2
(45) Date of Patent: Nov. 6, 2007

(54) ICE POWER PACK

(76) Inventors: Keith Eugene Peterman, 1401 Hollywood Pkwy., York, PA (US) 17403; Joshua Kurtz Peterman, 1401 Hollywood Pkwy., York, PA (US) 17403

( * ) Notice: Subject to any disclaimer, the term of this patent is extended or adjusted under 35 U.S.C. 154(b) by 0 days.

(21) Appl. No.: 10/233,391

(22) Filed: Sep. 3, 2002

(65) Prior Publication Data

US 2004/0122495 A1    Jun. 24, 2004

(51) Int. Cl.
*A61F 7/00*    (2006.01)
(52) U.S. Cl. ..................... 607/108; 607/114
(58) Field of Classification Search .............. 606/96, 606/108–114
See application file for complete search history.

(56) References Cited

U.S. PATENT DOCUMENTS

| | | | | |
|---|---|---|---|---|
| 740,847 A | * | 10/1903 | Glebsattel | 62/530 |
| 5,190,033 A | * | 3/1993 | Johnson | 607/108 |
| 5,314,005 A | * | 5/1994 | Dobry | 165/10 |
| 5,628,772 A | * | 5/1997 | Russell | 607/109 |

* cited by examiner

*Primary Examiner*—Roy D. Gibson
*Assistant Examiner*—Aaron Roane

(57) ABSTRACT

An improved cold/compress therapy for the treatment of muscle, tissue, tendon, or cartilage injury or damage. The ICE Power Pack consists of a plurality of hollow vessels filled with water or aqueous solutions or colloids that can be solidified in a conventional domestic or commercial freezer. The encapsulated water or aqueous solutions or colloids rely on the high latent heat of fusion as they undergo a phase change providing an extended therapeutic period in a medically safe temperature zone. The vessels are sandwiched between flexible insulating and non-insulating layers that serve as compresses.

13 Claims, 3 Drawing Sheets

ICE POWER PACK

BACKGROUND OF THE INVENTION

| | | | |
|---|---|---|---|
| 5,723,002 | 5,190,033 | 4,976,262 | 5,466,251 |
| 5,628,772 | 5,409,500 | 5,304,216 | 4,981,135 |
| 5,052,387 | 5,000,176 | 5,020,536 | |
| H759 | 4,688,572 | 4,628,932 | |

This invention relates to medical or sports cold/compress therapy and more specifically pertains to the combined use of the latent heat of fusion of water or other aqueous solutions coupled with a conformable compress to aid in the treatment and recovery of injured muscle, tissue, tendon, or cartilage.

It is widely accepted and well known that cooling an injured area along with mild compression of the same area is an effective means of limiting or reducing swelling and may also help to decrease recovery time. Generally, this is done by filling a plastic bag with ice and manually holding the bag in place and applying pressure. The two major problems with this are that it is inconvenient and messy. Many inventions have sought to alleviate either one or both of these problems through a variety of designs. Examples of these are laid out below and in the description of the ICE Power Pack system it will become evident how it improves on all of the following patents.

U.S. Pat. Nos. 4,628,932; 4,976,262; 5,000,176; 5.020, 536; 5,052,387; 5,466,251; 5,723,002 are all designs for holding an ice pack in place. These designs may all serve their function to secure an ice pack in one place but none of them make any reference to insulation which would allow the ice/cold pack to remain effective for a longer period of time. These designs also all require that the user manually fill and insert into the holder the cold pack which causes the ice packs to be inconvenient. Another problem with these inventions is that they only allow for the insertion of a minimal number of large ice/cold packs. This means that the water or slush contained within the cold/ice packs is free to move about and is thus unable to maintain constant intimate contact with the entire surface of the body part you wish to treat.

U.S. Pat. No. 5,190,033 uses a plurality of hollow spherical capsules filled with a gel or fluid that is chilled in a freezer or refrigerator. It fails to recognize the need to covert the fluid or gel to a solid. Solidifying the encapsulated water or aqueous solution is fundamental to our patent in order to take advantage of the heat of fusion of the solid. This patent has been abandoned for non-payment of maintenance fees.

U.S. Pat. No. 4,688,572 states that insulating the ice pack would "thwart the transfer of coldness to the injured limb." This statement is not supported by any further language indicating how this conclusion was reached and is both illogical and incorrect. The thermodynamic laws clearly show that heat is what is transferred, not coldness.

U.S. Pat. No. 4,981,135 is a design for a heating/cooling therapeutic thermal cuff that provides insulating layers and a means for securing the cuff to the body but the therapeutic inserts consist of a single bladder that has been quilted with parallel lines and thus does not allow for constant and direct contact on any bending joint such as a knee.

U.S. Pat. No. 5,304,216; H759; U.S. Pat. No. 5,409,500 are all designs for an ice pack and a holder but they have a common problem in that they specify the use of some sort of refrigerant gel that does not undergo a phase change and thus does not have a thermal plateau. The phase change is necessary for the cold pack to effectively treat an injured area at a constant medically safe temperature for extended periods of time.

U.S. Pat. No. 5,628,772 uses a plurality of balls within a plastic pouch but specifically requires the use of a gel, BlueIce.RTM, stating that it is better because an "ice/water solution rapidly attains the temperature of the underlying area being treated." This statement is incorrect. An ice/water equilibrium is maintained for long periods of time due to the extraordinarily high latent heat of fusion of ice. The lack of validity of the statement in this patent supports our claim that the ICE Power Pack System is a new and improved product. The Power Pack provides a significant therapeutic treatment period in the safe temperature zone, as compared to a gel such as BlueIce.RTM and other gels and slushes.

BRIEF SUMMARY OF THE INVENTION

The ICE Power Pack system is a new and improved cold therapy product for the treatment of muscle, tissue, tendon, or cartilage injury or damage. The ICE Power Pack system consists of a plurality of hollow vessels filled with water or aqueous solutions that can be solidified in a conventional domestic or commercial freezer. These vessels are contained in a pouch that consists of outer and inner layers composed of different materials. The interior layer of the ICE Power Pack system is a thin, elastic fabric which allows efficient transfer of heat from the injured area to the ICE Power Pack. This fabric also serves as a primary mild compress. The exterior layer consists of a thicker, flexible, insulating elastomer which helps extend effective therapy time by minimizing heat gain from the environment. The exterior layer also provides secondary support as a mild compress and holds the encapsulated spheres in place over the injured area. ICE Power Pack systems are anatomically engineered and specifically tailored to fit regions of the body which may experience injuries including designs for the hand, elbow, knee, torso, quadriceps/hamstrings, calf/shins, ankle, foot, neck, and shoulder. Most ICE Power Pack system designs are strategically held in place with Velcro.RTM. straps but may also be manufactured as a free floating design which does that does not include retaining straps. Not only does the ICE Power Pack alleviate or completely eliminate the specific problems associated with existing products as discussed above. The ICE Power Pack also solves many of the problems that plague the cold therapy market in general. These problems are:

1. Frostbite: "Frostbite" injuries are a significant concern with slush packs and gel packs because they rise very slowly from freezer temperature into a medically safe thermal zone. Slush packs and gel packs have a much higher specific heat in the "cold risk zone" than is found in the ICE Power Pack. To avoid this risk, some manufacturers recommend that a thin insulating layer such as a paper towel be placed between the skin and the pack. This helps avoid frostbite injuries but it also diminishes the heat absorbing capacity and therefore the effectiveness of these packs as cold therapy products is compromised. Frostbite risk becomes even greater when packs are stored in excessively cold freezer or if a slush or gel pack is compressed tightly against the skin without an insulating layer.

Advantage of ICE Power Pack: The ICE Power Pack system minimizes frostbite injuries since the specific heat of the encapsulated solid water is only 2.09 J/g. ° C. The ICE Power Pack quickly reaches a medically safe thermal zone.

2. Limited Effective Therapy Time: The main problem with all slush or gel packs is that they never reach a thermal plateau. They simply continue to rise in temperature from a "cold risk zone", through a safe "therapy zone", into a somewhat cold bit "ineffective zone". Thus, their effectiveness as a cold therapy is limited and diminishes with time.

Advantage of ICE Power Pack: The name "ICE Power Pack" was selected to emphasize its significantly extended time for effective Cold/Compress Therapy sessions. These extended sessions are a result of the high heat of fusion (334 J/g) for the encapsulated ice. In addition, a medically safe thermal plateau is maintained at 0° C. throughout the cold therapy session. The exterior layer limits heat gain from the exterior environment (i.e., minimizes cold loss) thus extending therapy session time.

The heating curve at FIG. 5 compares a medium Ace.RTM Gel Pack with an ICE Power Pack of the same size and mass. The two packs were placed side-by-side on separate pieces of 3 cm thick Styrofoam insulated boards at an ambient temperature of 21° C. Temperature was simultaneously monitored by placing digital readout thermometers between each pack and the Styrofoam board. Note the long thermal plateau of the ICE Power Pack. Also note the comparatively short effective therapy range of the Ace.RTM Gel Pack as well as the time spent in the frostbite range.

3. Lack of direct contact with injured area: Slush packs tend to remain rigid and not mold well to the contours of the body. Therefore, the actual points of contact are limited except for flat areas. Gel packs mold well to the contours of the body but the gel tends to flow into low areas in the pack due to gravity or squish away from areas where cold therapy is most needed due to applied pressure.

Advantage of ICE Power Pack: The small encapsulated geometric shapes easily mold to the contours of the body along with the thin interior layer. They are strategically held in place by the thick exterior insulating layer and straps. Most ICE Power Pack systems are engineered and designed for specific areas of the body.

4. The Mess and Inconvenience: Ice is frequently used to treat injuries by placing the ice in a plastic bag and manually holding it in place and applying pressure. The two major problems with this are that it is inconvenient and messy. As the ice melts it frequently leaks and creates messy puddles of water. This type of ice pack is also inconvenient in that it is not reusable.

Advantage of ICE Power Pack: The Power Pack system contain encapsulated ice, water, and solutions. Therefore as the encapsulated solution undergoes its phase change there is no leakage of the solution and consequently no mess. The ICE Power Pack is reusable by simply placing it in a freezer to recharge the system, allowing the user to once again take advantage of another extended cold/compress therapy session.

DETAILED DESCRIPTION OF THE INVENTION

Figure 1:
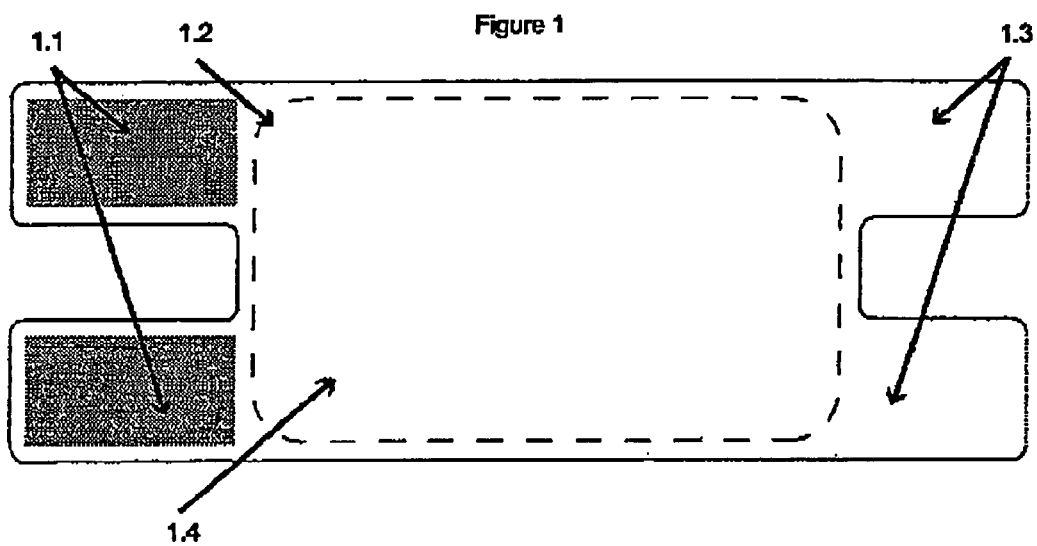
FIG. 1: This drawing shows a representative ICE Power Pack from the bottom.
  1.1: This section of the drawing shows the hook side of the Velcro.RTM that is used to secure the retaining straps.
  1.2: This represents the stitching that is used to secure the Ultrex.RTM inner layer to the outer layer of the ICE Power Pack.
  1.3: These Neoprene.RTM straps are the retaining system that secures the ICE Power Pack to the user. Note the straps extend out of both sides of the ICE Power Pack to ensure that the user will be able to achieve a maximum fit.
  1.4: This area outline by the stitching is the inner layer of the ICE Power Pack.
Figure 2:
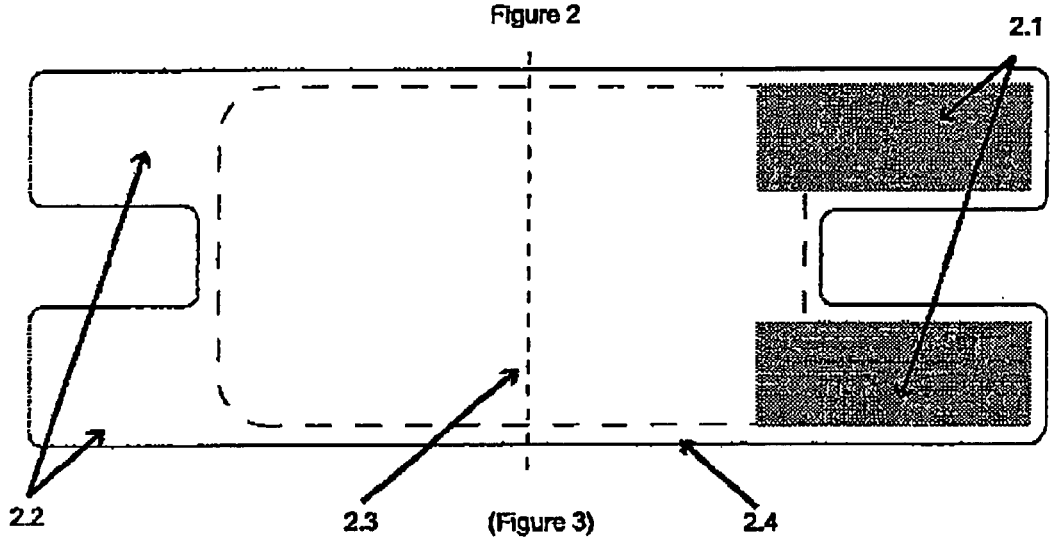
FIG. 2: This drawing shows a representative ICE Power Pack from the top.
  2.1: This section of the drawing shows the loop side of the Velcro.RTM that is used to secure the retaining straps.
  2.2: These are the opposing straps that allow the ICE Power Pack to be adjusted for a custom fit.
  2.3: This line displays the cross section that is illustrated in FIG. 3.
  2.4: The entire top layer of the ICE Power Pack is one piece and in this representative ICE Power Pack is constructed of Neoprene.RTM.
Figure 3:
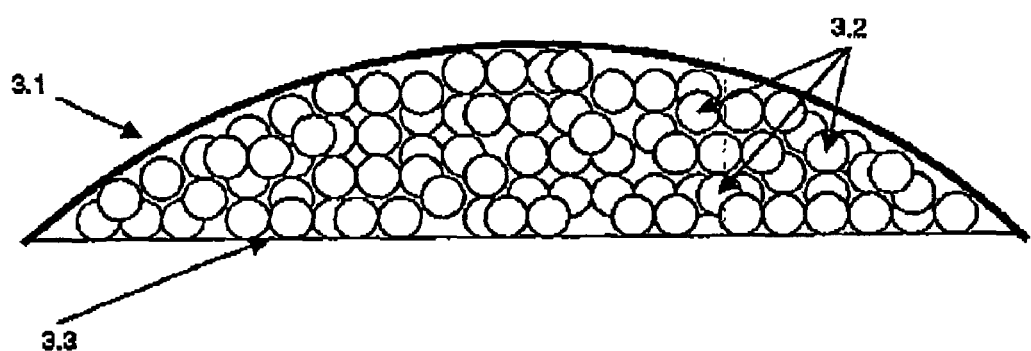
FIG. 3: This is a cross section of a representative ICE Power Pack.
  3.1: This is the top Neoprene.RTM layer of the ICE Power Pack.
  3.2: This is the plurality of water filled spheres that are enclosed in a pouch created by the inner and outer layers of the ICE Power Pack. Note that the spheres are of sufficient number that there is no empty space left within the pouch that would allow the spheres to migrate.
  3.3: This is the bottom Ultrex.RTM layer of the ICE Power Pack.
Figure 4:
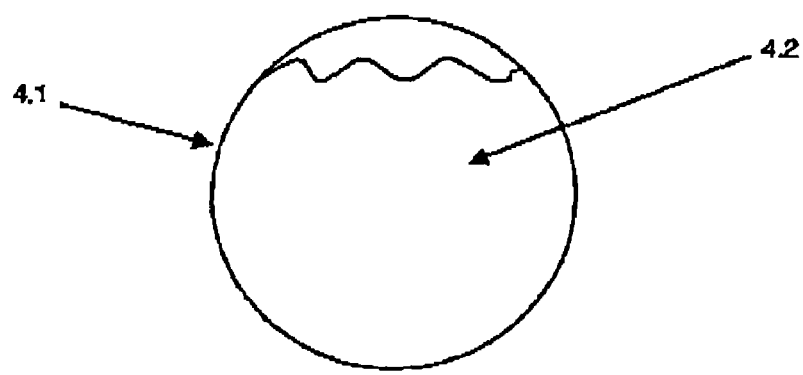
FIG. 4: This is an illustration of a single water filled plastic sphere.
  4.1: The wall of the representative sphere is constructed of plastic.
  4.2: The solution contained within the representative sphere is water and fills approximately 90% of the volume to allow for expansion of the water as it undergoes a phase change.
Figure 5:
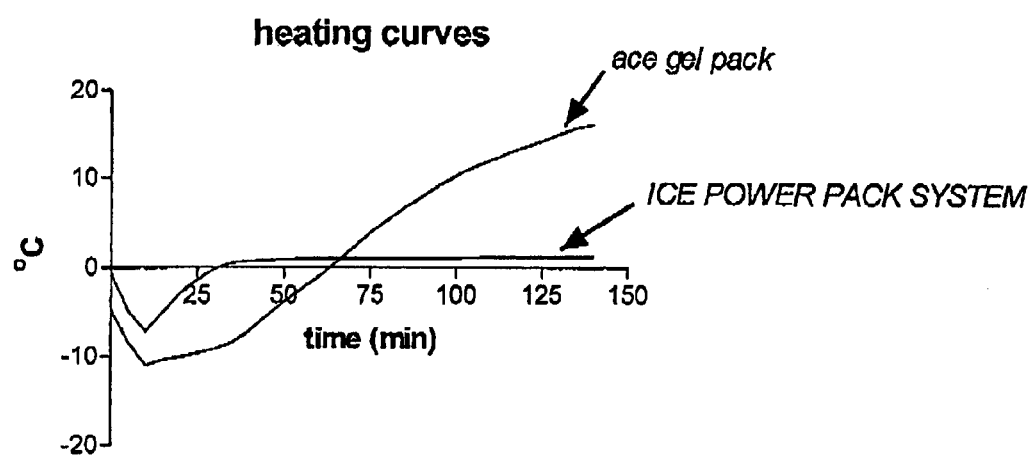
FIG. 5: This drawing charts a heating curve comparing a medium Ace.RTM Gel Pack with an ICE Power Pack of the same size and mass.

Introduction:

The principle of the ICE Power Pack system relies on fundamental concepts associated with phase changes. As a chemistry professor, one of the co-inventors (KEP) routinely asks the following question of his science and engineering majors when discussing physical properties of the states of matter.

The highest temperature of water drawn from the hot water tap in most homes is approximately 60° C. If 100 grams of hot tap water at 60° C. is added to 100 grams of ice at 0° C. in an insulated vessel, at what temperature will the system equilibrate?
  A. 0° C.
  B. Somewhere between 0 and 20° C.
  C. Somewhere between 20 and 40° C.
  D. Somewhere between 40 and 60° C.
  E. 60° C.

Nearly every student selects letter "C". The correct answer is "A".

The Principle:

The specific heat capacities of ice and liquid water are 2.09 J/g. ° C. and 4.18 J/g. ° C., respectively. However, the heat of fusion for ice is significantly higher, 334 J/g. This means that comparatively small amounts of energy are needed to warm ice to its freezing point or to warm liquid water to a higher temperature since these represent kinetic energy changes. A much larger amount of energy is required to convert the ice from its solid to its liquid phase since this represents a potential energy change that requires the breaking of hydrogen bonds.

The strength of intermolecular hydrogen bonds between water molecules with the concomitant high heat of fusion for water explains why the system referred to in the introduction thermally equilibrates at 0° C. In fact, calculations show that more than 20% of the original ice would still remain after it equilibrates.

Design:

The Power Pack system is a medical or sports cold/compress therapy product used to treat muscle, tissue, tendon, or cartilage damage. The principle of ICE or Ice/Compress/Elevation is well recognized as an immediate treatment for injuries, especially for sports injuries where athletes need to minimize recovery time. Immediate application of cold and a mild compress to an injured area followed by sustained elevation of the injured area with the cold/compress in place minimizes swelling thus aiding in the recovery process. The ICE Power Pack significantly improves on all cold/compress therapy products currently on the market.

The ICE Power Pack system consists of water or aqueous solutions or colloids encapsulated in polymeric cavities which are sandwiched between a flexible insulating outer layer and a flexible non-insulating inner layer. The polymeric encapsulating cavities may consist of single unit three dimensional geometries which pack efficiently and mold easily to the contours of the body. Single unit geometries may include but are not restricted to spheres, cylinders, "bucky balls", ellipsoids, etc. Both the outside and inside layers also serve as compresses.

Representative ICE Power Pack System

Materials:

Exterior layer: Consists of engineered and tailored Neoprene.RTM with Velcro.RTM straps. Neoprene.RTM was selected based on our experience as SCUBA divers. Neoprene.RTM has excellent insulating characteristics thus extending cold therapy sessions. It is flexible allowing it to be engineered and tailored to fit the target injury area. It is also an elastomer which allows it to serve as a secondary compress.

Interior Layer: Consists of tailored Ultrex.RTM a breathable waterproof fabric, which easily molds to the target injury area and allows efficient transfer of heat. It is elastic and serves as a mild primary compress.

Encapsulated Cavity: Consists of hollow plastic spheres (1 cm in diameter were used for the representative ICE Power Pack system illustrated in the drawings) with encapsulated distilled liquid water filling 90% of the volume. These spheres are inserted into the cavity of the pack in sufficient number as to prevent them from migrating within the cavity.

Manufacturing:

The process of manufacturing an ICE Power Pack is fairly simple and will be standard for the various designs of the packs. The only variations in manufacturing will be that in some designs the encapsulated cavities will be of a different shape, size, or number depending on which body part the particular pack is intended to treat. Also varying will be the shape of the pack in general (each pack is specifically tailored to fit a specific body part) including the main part of the pack and also the configuration, length, and placement of the retaining straps. The fabrics used for the inner and outer layers as well as the encapsulated vessels may also be altered.

Creating a pattern for the ICE Power Pack out of paper begins the manufacturing process. There will be two separate patterns. One pattern is created for the design of the outer layer of the pack and the other is created for the inner layer. Once the patterns are created the fabric (in this case Neoprene.RTM) for the outer layer is laid out and the pattern is placed over it. Then the outer layer is cut from the piece of fabric and set aside. Then the same is done for the inner layer (Ultrex.RTM was used for this representative pack). Once the two layers are cut out they are then assembled using a sewing machine. The inner layer is attached to the outer layer but a section of seam is left out to allow the insertion of the encapsulated vessels. Then the fastening system is attached to the strap portion of the outer layer (in this case Velcro.RTM). Once this is completed the pack is ready for the addition of the inner vessels. To prepare these vessels, 1 cm. in diameter plastic balls are each drilled in one place to allow the injection of distilled water. Then, using a syringe, the balls are filled to 90% volume with distilled water. The hole in each ball is then sealed using an epoxy. Then the balls are placed into the pouch that has been created between the inner and outer layer of the pack in sufficient number as to prevent them from migrating within the pouch. After this is completed the stitching is finished so that no balls can escape.

Note: This description of the manufacturing process is for hand assembly. The ICE Power Pack may also be manufactured using machines that perform the same steps but possibly at different stages and using different methods.

Use of the System:

The ICE Power Pack system is placed in a freezer typically at −10° C. or above for a period of at least 3 hours to assure that the encapsulated aqueous phase is in the solid state. When placed on an injured area, the encapsulated solid quickly warms to a safe 0° C. due to the small amount of heat (2.09 J/g. ° C.) needed to warm the encapsulated ice or solid solution. Once it reaches 0° C., the ICE Power Pack remains at 0° C. for an extended period due to the large enthalpy of fusion of ice trapped in the encapsulated spheres (334 J/g). The product name "ICE Power Pack" emphasizes its superiority over all competitor products on the market for cold therapy session time and its ability to maintain a thermal plateau at 0° C.

We claim:

1. A cold therapy pack for the treatment of muscle, tissue, tendon, or cartilage injury or damage comprising: a pouch that is specifically shaped to form to a body part; a plurality of hollow vessels that are filled with water or other aqueous solutions, that can be solidified in a conventional domestic or commercial freezer, contained within said pouch; said pouch is constructed of an elastic, flexible insulating outer layer constructed of neoprene that minimizes heat gain from the surrounding environment, wherein the external side neoprene outer layer that will not be in contact with the user's body is covered with a knit nylon fabric, and the internal side of the neoprene outer layer that will be in direct contact with the user's body is uncovered allowing the uncovered neoprene to grip the user's body thus reducing the ability of the cold therapy pack to shift or migrate during use; and a flexible waterproof, breathable, non-insulating inner layer that allows for effective transfer of heat from the area of the body being treated through the non-insulating inner layer to the cold therapy pack, wherein the inner layer, being constructed of waterproof, breathable, non-insulating fabric, allows condensation to escape while the water or other aqueous solution contained within the said plurality of vessels undergoes a phase change.

2. The cold therapy pack according to claim 1 where said plurality of vessels are preferably of a spherical shape but may also be cylinders, bucky balls, ellipsoids or any other geometric shape that would allow for efficient contouring to affected body part.

3. The cold therapy pack according to claim 1 where said plurality of vessels are constructed of plastic or other adequate material that allows for efficient transfer of heat.

4. The cold therapy pack according to claim 1 where said plurality of vessels within pouch are of substantial enough number as to prevent any empty spaces that would allow the plurality of vessels to migrate.

5. The cold therapy pack according to claim 1 wherein the outer layer, through its elastic properties, serves as a mild compress, prevents the pack from slipping or shifting position, and helps to prevent said plurality of vessels from migrating within said pouch.

6. The cold therapy pack according to claim 1 further comprising a releasable securing device for releasably securing the pack to the affected body part, wherein the securing device and the outer layer of the cold therapy pack are constructed of the same piece and type of material allowing for superior affixation and holding of the cold therapy pack to the body part being treated; securing straps, wherein because the securing device is constructed of the same piece of material as the external layer of the cold therapy pack, when the securing device straps are stretched to secure the pack to the user, the external layer of the cold therapy pack is also stretched and this causes the cold therapy pack to provide compression to the area being treated; and hook and loop fasteners that allow the securing straps to affix to each other or back to the main body of the cold therapy pack thus preventing the cold therapy pack from shifting while being used.

7. The cold therapy pack according to claim 1 wherein said pouch may also be quilted as necessary to prevent migration of the encapsulated vessels when a large number of the vessels alone is not sufficient to prevent migration.

8. A cold therapy pack for the treatment of muscle, tissue, tendon, or cartilage injury or damage comprising: a pouch that is specifically shaped to form to a body part; a plurality of hollow vessels that are filled with water or other aqueous solutions, that can be solidified in a conventional domestic or commercial freezer, contained within said pouch; said pouch is constructed of an elastic, flexible insulating outer layer constructed of neoprene that minimizes heat gain from the surrounding environment, wherein the external side neoprene outer layer that will not be in contact with the user's body is covered with a knit nylon fabric, and the internal side of the neoprene outer layer that will be in direct contact with the user's body is uncovered allowing the uncovered neoprene to grip the user's body thus reducing the ability of the cold therapy pack to shift or migrate during use; a flexible waterproof, breathable, non-insulating inner layer that allows for effective transfer of heat from the area of the body being treated through the non-insulating inner layer to the cold therapy pack, wherein the inner layer, being constructed of waterproof, breathable, non-insulating fabric, allows condensation to escape while the water or other aqueous solution contained within the said plurality of vessels undergoes a phase change; a releasable securing device for releasably securing the pack to the affected body part, wherein the securing device and the outer layer of the cold therapy pack are constructed of the same piece and type of material allowing for superior affixation and holding of the cold therapy pack to the body part being treated; securing straps, wherein because the securing device is constructed of the same piece of material as the external layer of the cold therapy pack, when the securing device straps are stretched to secure the pack to the user, the external layer of the cold therapy pack is also stretched and this causes the cold therapy pack to provide compression to the area being treated; and hook and loop fasteners that allow the securing straps to affix to each other or back to the main body of the cold therapy pack thus preventing the cold therapy pack from shifting while being used.

9. The cold therapy pack according to claim 8 where said plurality of vessels are preferably of a spherical shape but may also be cylinders, bucky balls, ellipsoids or any other geometric shape that would allow for efficient contouring to affected body part.

10. The cold therapy pack according to claim 8 where said plurality of vessels are constructed of plastic or other adequate material that allows for efficient transfer of heat.

11. The cold therapy pack according to claim 8 where said plurality of vessels within pouch are of substantial enough number as to prevent any empty spaces that would allow the plurality of vessels to migrate.

12. The cold therapy pack according to claim 8 where the outer layer, through its elastic properties, serves as a mild compress, prevents the pack from slipping or shifting position, and helps to prevent said plurality of vessels from migrating within said pouch.

13. The cold therapy pack according to claim 8 wherein said pouch may also be quilted as necessary to prevent migration of the encapsulated vessels when a large number of the vessels alone is not sufficient to prevent migration.

* * * * *